United States Patent
Sundman

(10) Patent No.: US 10,682,337 B2
(45) Date of Patent: Jun. 16, 2020

(54) COMPOSITIONS AND METHODS FOR TREATMENT AND PREVENTION OF PYREXIA IN HORSES

(71) Applicant: Kindred Biosciences, Inc., Burlingame, CA (US)

(72) Inventor: Emily Sundman, Burlingame, CA (US)

(73) Assignee: Kindred Biosciences, Inc., Burlingame, CA (US)

( * ) Notice: Subject to any disclaimer, the term of this patent is extended or adjusted under 35 U.S.C. 154(b) by 52 days.

(21) Appl. No.: 15/554,568

(22) PCT Filed: Mar. 2, 2016

(86) PCT No.: PCT/US2016/020463
§ 371 (c)(1),
(2) Date: Aug. 30, 2017

(87) PCT Pub. No.: WO2016/141065
PCT Pub. Date: Sep. 9, 2016

(65) Prior Publication Data
US 2018/0071256 A1 Mar. 15, 2018

Related U.S. Application Data

(60) Provisional application No. 62/127,401, filed on Mar. 3, 2015.

(51) Int. Cl.
| | |
|---|---|
| *A61K 31/4152* | (2006.01) |
| *A61K 47/38* | (2006.01) |
| *A61K 9/06* | (2006.01) |
| *A61K 9/08* | (2006.01) |
| *A61K 47/36* | (2006.01) |
| *A61K 47/10* | (2017.01) |
| *A61K 47/14* | (2017.01) |

(52) U.S. Cl.
CPC ............ *A61K 31/4152* (2013.01); *A61K 9/06* (2013.01); *A61K 9/08* (2013.01); *A61K 47/10* (2013.01); *A61K 47/14* (2013.01); *A61K 47/36* (2013.01); *A61K 47/38* (2013.01)

(58) Field of Classification Search
CPC .... A61K 31/4152; A61K 47/14; A61K 47/10; A61K 47/38; A61K 9/08; A61K 9/06; A61K 47/36
See application file for complete search history.

(56) References Cited

U.S. PATENT DOCUMENTS

| | | |
|---|---|---|
| 2007/0043120 A1 | 2/2007 | Beyreuther et al. |
| 2011/0212926 A1 | 9/2011 | Muhammad et al. |
| 2013/0178453 A1* | 7/2013 | Rohde ................ C07D 491/048 514/171 |

FOREIGN PATENT DOCUMENTS

| | | | |
|---|---|---|---|
| DE | 199 20 415 | 11/2000 | |
| WO | WO-0025750 A1 * | 5/2000 | ........... A61K 9/2013 |
| WO | WO 2008/115572 | 9/2008 | |

OTHER PUBLICATIONS

Nikolova et al (Biotechnol. & Biotechno.Eq., 26(6), 3329-3337) (Year: 2012).*
Volz et al (Br.J.Clin.Pharmacol., Oct. 1980; 10 Suppl 2:299S-308S) (Year: 1980).*
International Search Report and Written Opinion in PCT/US2016/020463, dated May 20, 2016, 15 pages.
Abutarbush et al., "Evaluation of the use of Atropine Sulfate, a Combination of Butylscopolammonium Bromide and Metamizole Sodium, and Flunixin Meglumine to Ameliorate Clinical Adverse Effects of Imidocarb Dipropionate in Horses," AJVR, 2013, 74(11):1404-1408.
Aupanun et al., "Pharmacokinetic Assessment of the Marker Active Metabolites 4-Methyl-amino-antipyrine and 4-Acetyl-amino-antipyrine After Intravenous and Intramuscular Injection of Metamizole (Dipyrone) in Healthy Donkeys," Journal of Equine Veterinary Science, 2016, 47:55-61.
Etcheverry et al., "Equine Infectious Anemia Diagnosis in a 3 Months Old Foal," Journal of Equine Veterinary Science, 2016, 39:S42-43.
Giorgi et al., "Pharmacokinetic Profiles of the Active Metamizole Metabolites in Healthy Horses," J. Vet. Pharmacol. Therap., 2017, 40(2):165-171.
Klimczak et al., "Immunostimulant Quickly Aids Weanling ERDC Cases," Journal of Equine Veterinary Science, 1992, 12(2): 68-69.
Extended European Search Report from European Application No. 16759415.9, dated Oct. 9, 2018, 9 pages.

* cited by examiner

*Primary Examiner* — Sudhakar Katakam
(74) *Attorney, Agent, or Firm* — McNeill Baur PLLC

(57) ABSTRACT

Methods for treating and preventing pyrexia and other diseases in equines such as horses involving administering an oral pharmaceutical formulation containing metamizole are disclosed.

17 Claims, 1 Drawing Sheet

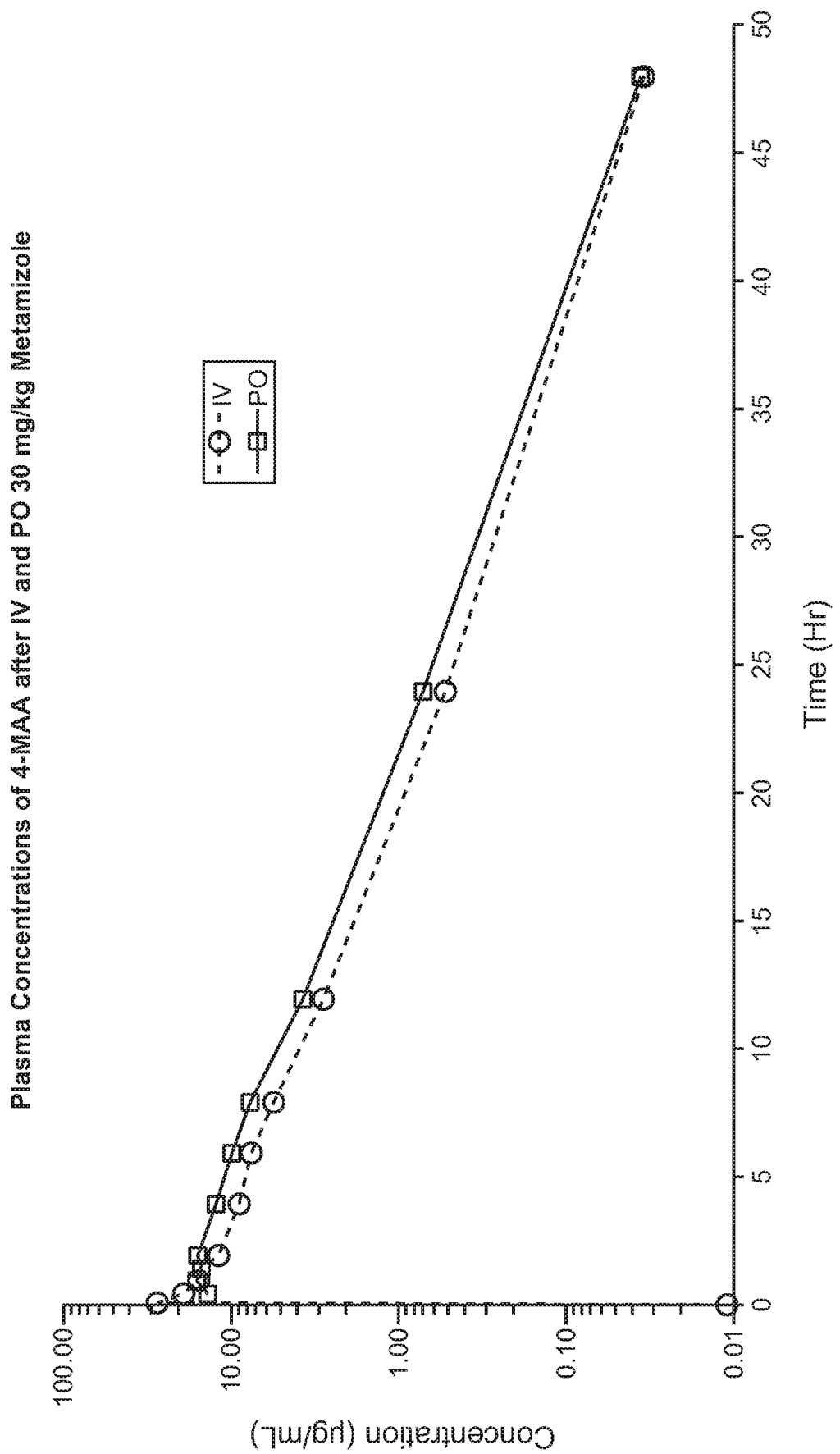

COMPOSITIONS AND METHODS FOR TREATMENT AND PREVENTION OF PYREXIA IN HORSES

This application claims the benefit of priority to U.S. Provisional Application No. 62/127,401, filed Mar. 3, 2015, which is incorporated by reference herein in its entirety for any purpose.

FIELD

The present disclosure provides new pharmaceutical formulations, delivery and treatment methods for administering metamizole and its pharmaceutically acceptable salts to non-human animals, particularly equines, for therapeutic purposes, including but not limited to the treatment and prevention of pyrexia. The present disclosure also provides a process for the preparation of the new pharmaceutical formulations.

BACKGROUND

Pyrexia (fever) is common to all mammals, including equines such as horses. Pyrexia is an elevation in core body temperature above the normal range due to an increase in the temperature regulatory set-point. Pyrexia can be caused by many medical conditions ranging from non-serious to potentially serious and even life threatening. These include viral, bacterial, and parasitic infections, such as equine encephalomyelitis, equine influenza, equine herpes virus, West Nile virus, strangles, and Potomac horse fever. Physical trauma and stress can also cause a fever in a horse. While a fever can be a useful defense mechanism, since the body's immune response can be strengthened at higher temperatures, very high body temperatures, particularly for prolonged periods of time, can pose significant health risks to the patient. In the setting of animal and human healthcare, it often becomes necessary to reduce a patient's temperature to a safer range (e.g., treat the patient's fever) by medical intervention. Some of the most common causes of illness in horses are febrile diseases, such as respiratory infections, certain forms of colic, post-vaccination reactions, and tick- and mosquito-borne infections).

The treatment of pyrexia in horses and foals by parenteral administration of the nonsteroidal anti-inflammatory drug (NSAID) metamizole is known in the art. Metamizole products are marketed in some countries under the generic name dipyrone and a variety of brand names including, but not limited to Vetalgin® as an antipyretic, analgesic, and anti-inflammatory agent. Currently available veterinary formulations of metamizole require parenteral (i.e., intramuscular, intravenous (IV), or subcutaneous) administration, with IV administration being the usual route. The oral formulations of metamizole available in the veterinary market for dogs are not suitable for administration to horses due to a variety of factors including dose. Obtaining an oral dosage form of metamizole of sufficiently high concentration to treat a large animal such as a horse is itself technically challenging, but to further do so (i) in an oral format that facilitates the horses actually ingesting the drug as opposed to expelling it from the mouth prior to ingestion, and (ii) in an oral format that is stable at the temperatures typically found in a barn environment, is even more so.

Parenteral administration of metamizole in horses presents many difficulties, however, and there is a need for simpler methods for treating pyrexia. Horses have large jugular veins that, when healthy, are simple to access. However, other peripheral vessels are much more challenging. Access to jugular veins can be limited for numerous reasons, including but not limited to thrombosis, poor temperament, and localized dermal disease. Once the jugular veins are inaccessible, intravenous administration of medication to a horse is extremely challenging. Moreover, in some instances, an unintended peri-vascular administration of metamizole to an equine may result in adverse effects, including, but not limited to, thrombophlebitis. This is true of NSAIDs, like metamizole, generally. Further complications can arise due to, in many instances, medications being administered to horses by non-veterinary personnel. These individuals often lack the training and experience to administer parenteral medications safely. Additionally, many medications are administered repeatedly or chronically, which may lead to thrombosis of the vein. Finally, the equine patient may also develop evasive behaviors, so repeat parenteral administration of any medication can be challenging for that reason alone.

For these and other reasons, there exists an unmet need for veterinary formulations of metamizole suitable for oral administration to equines to treat pyrexia that avoid difficulties commonly known and experienced with the currently available parenteral formulations. There further exists an unmet need for oral veterinary formulations of metamizole that can be easily and readily administered to a horse, even by unskilled caretakers who are not veterinarians. Such formulations and methods for using and administering them are provided by the present disclosure.

SUMMARY

The present disclosure provides methods for the prevention of pyrexia and other diseases in horses by oral administration of a therapeutically effective amount of metamizole. Typically, the therapeutically effective amount for an adult horse will be a unit dose of the therapeutic formulation sufficient to administer an oral dose of metamizole in the range of 10-60 mg of metamizole per kg of subject weight, i.e., typically about 25-50 mg/kg or 30-40 mg/kg, and so for the typical 350 kg to 1000 kg adult mare, a typical therapeutically effective (single) dose administered at, e.g., 30 mg/kg would be in the range 10.5 g to 30 g. For a foal, the therapeutically effective amount will be a unit dose of the therapeutic formulation sufficient to administer an oral dose of metamizole in the range of 10-50 mg of metamizole per kg of subject weight, i.e., typically about 15-40 mg/kg, and so for the typical foal (for example, weighing approximately 35-100 kg), a typical therapeutically effective (single) dose administered at, e.g., 20 mg/kg would be in the range of 700 to 2000 mg. The present disclosure also provides oral formulations of metamizole. In these oral formulations, the concentration of metamizole ranges from about 200 to 750 mg/ml, making the dose of a typical formulation, i.e., where the metamizole is present at 500 mg/ml, for the typical adult mare in the range of 20 to 100 ml, which can easily be administered using for example a syringe for depositing the dose in the horse's mouth. The formulations of the present disclosure include, but are not limited to, materials viscous enough to remain in the mouth after administration, and include paste and gel formulations.

In some embodiments, a pharmaceutical composition comprising 200 mg/ml to 750 mg/ml, or 250 mg/ml to 750 mg/ml, or 400 mg/ml to 600 mg/ml, metamizole is provided, wherein the pharmaceutical composition is for oral administration to equines. In some embodiments, the pharmaceutical composition is a gel or paste. In some embodiments, said gel or paste comprises hydroxypropylcellulose, for example, at a concentration of 10 to 50 mg/ml, or 10 to 40 mg/ml, or 10 to 30 mg/ml, or 15 to 25 mg/ml. In some embodiments, said gel or paste comprises at least one paraben. In some embodiments, said gel or paste comprises methyl paraben and/or propyl paraben, or methyl paraben and propyl paraben. In some embodiments, the total parabens are present at a concentration of 0.1 to 5 mg/ml, or 0.5 to 5 mg/ml, or 1 to 3 mg/ml.

In some embodiments, a pharmaceutical composition for oral administration of metamizole to equines is provided, wherein the pharmaceutical composition comprises at least one polymeric excipient. In some embodiments, the at least one polymeric excipient is selected from albumin, acacia, alginic acid (or alginate salts, e.g. sodium alginate), bentonite, carbomers, carboxymethylcellulose, carrageenan, cellusoses, cellulose ethers, chitosan derivatives, dextran, divinyl ether-maleic anhydride (DIVEMA), dydroxyethylcellulose, ethylcellulose, gelatin, guar gum, hyaluronic acid (HA), hydroxyethylcellulose, hydroxypropylcellulose, hydroxypropylmethylcellulose, methylcellulose, N-(2-Hydroxypropyl) methacrylamide (HPMA), magnesium aluminum silicate, methylcellulose, pectins, polyacrylamides, polyacrylic acid (PAA), polyethylene glycol (PEG) and PEG conjugates, polyethylene oxides, polyoxamers, polyoxazoline, polyphosphates, polyphosphazenes, polyvinyl alcohol (PVA), polyvinyl pyrrolidone (PVP), polyvinyl pyrrolidone-vinyl acetate (PVP-VA), starch or starch based derivatives, tragacanth, and xanthan gum. In some embodiments, the pharmaceutical composition for oral administration of metamizole to equines comprises xanthan gum. In some embodiments, the xanthan gum is present at a concentration of 1 mg/ml to 50 mg/ml, or 1 mg/ml to 40 mg/ml, or 1 mg/ml to 30 mg/ml, or 1 mg/ml to 20 mg/ml, or 5 mg/ml to 20 mg/ml, or 5 mg/ml to 15 mg/ml.

In some embodiments, a pharmaceutical composition for oral administration of metamizole to equines is provided, wherein the pharmaceutical composition comprises at least one preservative agent. In some embodiments, the preservative agent is selected from alcohol, benzyl alcohol, bronopol, chlorbutol, chlorocreson, a paraben such as, without limitation, butyl, methyl or propyl paraben, phenol, phenylethanol, sodium benzoate, potassium sorbate, sorbic acid, glycerin, and propylene glycol. In some embodiments, the pharmaceutical composition for oral administration of metamizole to equines comprises propylene glycol. In some embodiments, the propylene glycol is present at a concentration of 10 mg/ml to 500 mg/ml, or 10 mg/ml to 300 mg/ml, or 50 mg/ml to 300 mg/ml, or 50 mg/ml to 200 mg/ml, or 50 mg/ml to 150 mg/ml.

In some embodiments, a gel or paste comprising 200 mg/ml to 750 mg/ml, or 250 mg/ml to 750 mg/ml, or 400 mg/ml to 600 mg/ml metamizole is provided, wherein the gel or paste comprises xanthan gum, for example, at a concentration of 1 mg/ml to 50 mg/ml, or 1 mg/ml to 40 mg/ml, or 1 mg/ml to 30 mg/ml, or 1 mg/ml to 20 mg/ml, or 5 mg/ml to 20 mg/ml, or 5 mg/ml to 15 mg/ml. In some embodiments, the gel or paste comprises propylene glycol, for example, at a concentration of 10 mg/ml to 500 mg/ml, or 10 mg/ml to 300 mg/ml, or 50 mg/ml to 300 mg/ml, or 50 mg/ml to 200 mg/ml, or 50 mg/ml to 150 mg/ml.

In some embodiments, the pharmaceutical composition provided herein comprises 500 mg/mL metamizole sodium monohydrate, 10 mg/ml xanthan gum, and 100 mg/ml propylene glycol, in an aqueous solution.

In various embodiments, methods of treating an equine with pyrexia are provided, said method comprising orally administering a therapeutically effective dose of metamizole to said equine. In some embodiments, said dose is in the range of 25 mg metamizole per kg of equine subject weight (mg/kg) to 40 mg/kg, or in the range of 30 mg metamizole per kg of equine subject weight (mg/kg) to 35 mg/kg. In some embodiments, following administration of the oral metamizole, the equine's temperature is reduced by at least 1° C. or at least 1.5° C. or at least 2° C. six hours after administration of metamizole. In some embodiments, following administration of the oral metamizole, the equine's temperature is reduced by at least 1° C. or at least 1.5° C. or at least 2° C. six hours after administration of the first dose of metamizole. In various embodiments, the temperature is rectal temperature.

Thus, in some embodiments, the present disclosure provides various oral formulations and methods of using such formulations in treatments for controlling fever and other diseases in horses. The methods include administering e.g., once, several times, or periodically, a therapeutically effective amount of metamizole by oral administration to a horse. In certain embodiments, the oral formulation is a formulation described herein. The present disclosure further includes, in various embodiments, various veterinary oral formulations of metamizole, as well as various methods of treatment.

One aim of the present disclosure was a pharmaceutical formulation of metamizole that could be easily administered in a therapeutically effective amount to an equine. Example 1, below, demonstrates how this object of the disclosure was achieved using simple aqueous formulations of metamizole administered orally to horses. Because veterinarians and caretakers generally prefer more viscous formulations of orally administered medications intended for use in horses, however, the present disclosure also provides oral formulations comprising one or more gels or other thickening agents. In one important aspect, a pharmaceutical gel or paste formulation is provided comprising a therapeutically effective amount of metamizole and having a viscosity such that is can be easily drawn into a syringe and, after the desired dose is administered by deposition in a horse's mouth, will remain there long enough for the desired dose to be consumed.

SUMMARY OF THE DRAWINGS

FIG. 1 is a chart showing the results of metamizole bioavailability for oral and intravenous dosage forms that have been administered to horses at a dose of 30 mg/kg, as described in Example 1.

DETAILED DESCRIPTION

In one aspect, the present disclosure provides a pharmaceutical formulation of metamizole that is a gel or paste or other pharmaceutical formulation intended for oral administration. This aspect of the disclosure arose in part from the surprising discovery that metamizole could be effectively dosed orally, in combination with overcoming the challenges associated with successfully administering therapeutically effective levels of metamizole orally to a horse. These challenges included developing a gel or paste formulation, as a solution or other liquid formulation of insufficient viscosity would be at risk of loss after administration, due to the nature of the horse's mouth and throat. The present disclosure provides novel gel and paste formulations of metamizole that have sufficiently high viscosity to remain in place after oral administration and to deliver therapeutically effective doses. To facilitate description of the invention and better appreciation of its advantages, the following definitions are provided.

Definitions

Unless defined otherwise below, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

The term "about" as used herein refers to greater or lesser than the value or range of values stated by 1/10 of the stated values, but is not intended to limit any value or range of values to only this broader definition. For instance, a value of "about 30%" means a value of between 27% and 33%. Each value or range of values preceded by the term "about" is also intended to encompass the embodiment of the stated absolute value or range of values. Recitation of ranges of values herein are merely intended to serve as a shorthand method of referring individually to each separate value inclusively falling within the range, unless otherwise indicated herein, and each separate value is incorporated into the specification as if it were individually recited herein.

The phrase "bulking agent" refers to an excipient suitable for use in a pharmaceutical formulation that is inert and simply provides the product with more mass than it would have otherwise. Suitable bulking agents for use in the pharmaceutical formulations include, without limitation, polyethylene glycol (PEG), such as PEG 400 and PEG 3350.

The phrase "colloidal dispersion" refers to a material in which particles of colloidal dimension (i.e., typically between 1 nm and 1 μm) are distributed uniformly throughout a liquid.

The term "cream" refers to a type of emulsion, comprising at least two immiscible liquid phases, one dispersed in the form of drops or droplets within the other. Creams typically are intended for external application to the skin or mucous membranes.

The term "gel" as used herein refers to a material that is safe for oral administration to an equine such as a horse that is a semisolid dosage form that contains a gelling agent to provide stiffness to a solution or a colloidal dispersion. A gel may contain suspended particles.

The term "metamizole" (also known as "dipyrone") as used herein refers to [(2,3-dihydro-1,5-dimethyl-3-oxo-2-phenyl-1H-pyrazol-4-yl)methylamino] methanesulfonic acid and its pharmaceutically acceptable salts. Metamizole is available commercially (e.g., BOC Sciences) and generally has the structure shown in Formula I:

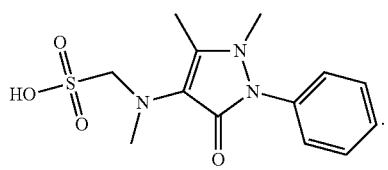 [SMILES: Cc1c(N(C)CS(=O)(=O)O)c(=O)n(-c2ccccc2)n1C]

Any reference to metamizole herein impliedly refers to any pharmaceutically acceptable salt, polymorph, crystal, or pro-drug form thereof. Metamizole and metamizole sodium and metamizole sodium monohydrate are known compounds in the art and methods for their preparation may be found in the literature. An exemplary pharmaceutically acceptable salt of metamizole is the sodium salt having the structure in Formula II:

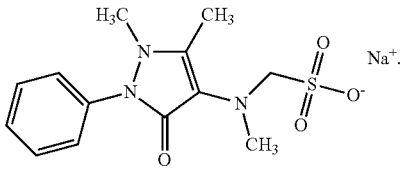 [SMILES: Cc1c(N(C)CS(=O)(=O)[O-])c(=O)n(-c2ccccc2)n1C]

Metamizole sodium monohydrate is metamizole sodium with a single water molecule associated with the metamizole sodium. In various embodiments provided herein, the stable active metabolite of metamizole, 4-methylaminoantipyrine (4-MAA), may be used in place of metamizole in the pharmaceutical compositions provided herein.

The term "ointment" refers to a pharmaceutical formulation that is a semisolid preparation intended for external application to the skin or mucous membranes and includes compositions derived from four "ointment bases," which are hydrocarbon bases, absorption bases, water-removable bases, and water-soluble bases. The Merck Veterinary Manual defines "ointment" as a greasy, semi-solid preparation that contains dissolved or dispersed drug. Ointment bases include hydrocarbons, vegetable oils, silicones, absorption bases consisting of a mixture of hydrocarbons and lanolin, emulsifying bases consisting of a mixture of hydrocarbons and an emulsifying agent, and water-soluble bases. Ointment bases influence topical drug bioavailability by (i) their occlusive properties that hydrate the stratum corneum, which can enhance drug flux across the skin; and (ii) their properties that affect drug dissolution within the ointment and drug partitioning from the ointment to the skin.

The term "paste" refers to a pharmaceutical formulation that is a semisolid preparation of stiff consistency intended for external application to the skin, oral cavity, or mucous membranes and is a semisolid dosage form containing a large proportion (20-50%) of solids finely dispersed in a fatty vehicle.

The phrase "pharmaceutical formulation" refers to a composition intended for therapeutic use that is safe and effective for its intended use. A formulation safe and effective for one type of use, such as topical application, may not be safe or effective for another type of use, such as IV administration. Thus, a "pharmaceutical formulation for topical administration", for example, excludes any type of pharmaceutical formulation that would not be safe or effective for its intended use.

The term "preservative" refers to an excipient suitable for use in a pharmaceutical formulation, such as an ointment, that functions to maintain the drug in a desired physical state. A preservative may have anti-microbial or anti-oxidant properties or may otherwise serve to protect the drug, e.g., from exposure to light or air. Suitable preservatives include parabens such as, without limitation, butyl, methyl or propyl paraben; sodium metabisulfate; potassium sorbate; sorbic acid; and butylated hydroxytoluene (BHT).

The term "pyrexia" refers to an elevation in body temperature (i.e., a fever) that is believed by a physician or veterinarian to require medical intervention to lower, e.g., to a safe set-point.

The term "semisolid" refers to a material that is not pourable; it does not flow or conform to its container at room temperature. It does not flow at low shear stress and generally exhibits plastic flow behavior.

The term "solubilizer" refers to an excipient suitable for use in a pharmaceutical formulation, such as an ointment, that facilitates dissolution of a drug into another substance. Suitable solubilizers for use in the pharmaceutical formulations provided herein include, without limitation, DGME, Labrasol®, and oleyl alcohol.

The term "solution" refers to a homogenous liquid preparation that contains one or more chemical substances dissolved in one or a mixture of miscible solvents.

The phrase "therapeutically effective dose" refers to that amount of a drug (an "active pharmaceutical ingredient" or "API") that is administered simultaneously or contemporaneously in one administration (multiple unit dose forms, i.e., pills, tablets, capsules, injections, liquids, pastes can be administered in one administration) to achieve a desired therapeutic outcome, even if multiple administrations over time are administered in the course of therapy.

In various embodiments, the metamizole is used in a pharmaceutical formulation for oral administration to a horse to prevent or treat pyrexia. In various preferred embodiments, the metamizole is orally administered in the form of a gel. A therapeutically effective dose of metamizole for practice of the methods provided herein is in the range of 25 mg to 40 mg metamizole/per kg weight of animal (mg/kg)/per dose. Typically, the therapeutically effective dose is administered only once, or no more than a few times, daily, and daily administration continues for several days or longer, but single day treatments can be effective in some animals for some purposes. Generally, however, treatment will continue on consecutive days for several days to a week, or longer. The dose may be adjusted using kg of weight of the animal to be treated. In some embodiments, oral administration with a gel formulation provided herein is continued for 2, 3, 5, 7, or more consecutive days.

The phrases "thickening agent" and "gelling agent" as used herein refers to any pharmaceutically acceptable substance that can increase the viscosity of a liquid without substantially changing its other desired properties.

In some embodiments, the present disclosure provides a pharmaceutical formulation that is a gel, paste or other suitable semi-solid form that can be placed in the mouth of the horse, i.e., with an applicator such as a syringe or spatula, to provide for oral ingestion of the formulation when the animal swallows the material. In preferred embodiments, however, the formulation is a gel that is placed in the animal's mouth so that it is consumed orally. Thus, in some embodiments the present disclosure provides a pharmaceutical formulation that is gel or other suitable semi-solid form that can be orally administered.

The present disclosure provides new oral pharmaceutical formulations comprising metamizole. In some embodiments, the present disclosure provides a pharmaceutical formulation of metamizole for oral administration comprising a therapeutically effective amount of metamizole, such as metamizole sodium or metamizole sodium monohydrate, and a thickening agent, and optionally a flavoring. In some embodiments, the thickening agent is a polymer or a monomer and a gelling agent or an admixture of any and all.

In some embodiments of the present disclosure, the pharmaceutical composition contains metamizole at a concentration sufficiently high to enable dosing at 25-40 mg/kg, i.e., concentrations in the range of about 200 mg/ml to 750 mg/ml, or 250 mg/ml to 750 mg/ml. Typically, the administered dose will be in the range of from about 10 to 50 mg/kg, or 10 to 40 mg/kg, or 20 to 50 mg/kg, or 20 to 40 mg/kg, or 10 mg/kg to 35 mg/kg, or 10 to 30 mg/kg, or 15 to 35 mg/kg, or 15 to 30 mg/kg. In some embodiments of the present disclosure the pharmaceutical composition contains metamizole in a range of about 25% w/w to 50% w/w.

In some embodiments, the therapeutically effective unit dose has a volume of from about 10 to 100 ml, or about 10 to 75 ml, or about 10 to 50 ml, and preferably of 20 ml to 30 ml.

In some embodiments, the therapeutically effective dose is 30 mg/kg and the concentration of metamizole in the oral dose formulation is 500 mg/ml.

The oral formulations provided herein generally have a viscosity higher than that of, for example and without limitation, the Vetalgin (Intervet) metamizole product for IV administration, which, as shown in the examples can be orally administered in accordance with the present disclosure to treat pyrexia. The desired viscosity is in the range of that of a semisolid, i.e., a gel or paste, which enables the administrator of the drug to place a therapeutically effective dose in the horse's mouth with confidence that it will be consumed rather than wash out of the horse's mouth as a solution would.

The desired viscosity is at least about 200 centipoise (cps) to 30,000 cps, of 200 cps to 20,000 cps, or 500 cps to 10,000 cps, or 1,000 cps to 7,000 cps, at 25° C. In some embodiments, the pharmaceutical composition comprises a thickening agent in a concentration sufficient to achieve a final viscosity of greater than 500 cps and less than 10,000 cps at 25° C.

This viscosity may be achieved by using a variety of pharmaceutically acceptable polymeric excipients or other thickening agents and/or gelling agents, illustrative examples of which are described below, such that the novel formulations provided herein are typically in the form of a gel administered using a syringe (a paste could similarly be prepared and administered orally). A typical novel gel formulation thus contains metamizole, water, and at least one (and typically two or more) pharmaceutically acceptable polymeric excipients that together with the formulation conditions used to prepare the gel, provide a gel of the desired viscosity.

Suitable pharmaceutically acceptable polymeric excipients include, for example and without limitation, albumin, acacia, alginic acid (or alginate salts, e.g. sodium alginate), bentonite, carbomers, carboxymethylcellulose, carrageenan, cellusoses, cellulose ethers, chitosan derivatives, dextran, divinyl ether-maleic anhydride (DIVEMA), dydroxyethylcellulose, ethylcellulose, gelatin, guar gum, hyaluronic acid (HA), hydroxyethylcellulose, hydroxypropylcellulose, hydroxypropylmethylcellulose, methylcellulose, N-(2-Hydroxypropyl) methacrylamide (HPMA), magnesium aluminum silicate, methylcellulose, pectins, polyacrylamides, polyacrylic acid (PAA), polyethylene glycol (PEG) and PEG conjugates, polyethylene oxides, polyoxamers, polyoxazoline, polyphosphates, polyphosphazenes, polyvinyl alcohol (PVA), polyvinyl pyrrolidone (PVP), polyvinyl pyrrolidone-vinyl acetate (PVP-VA), starch or starch based derivatives, tragacanth, and xanthan gum. Those of skill in the art will appreciate that these polymers may variously be called gelling agents or thickening agents in the art and that any pharmaceutically acceptable gelling agent or thickening agent may be used in a gel or paste formulation, including, in particular, as substitutes for all or some portion of or in addition to the polymeric excipient(s) specifically exemplified in the illustrative novel embodiments of certain formulations described in the examples below.

In various embodiments, the oral pharmaceutical formulation contains hydroxypropyl cellulose (HPC) and/or a paraben. In some such embodiments, HPC may be present at a concentration of 10 to 50 mg/ml, or 10 to 40 mg/ml, or 10 to 30 mg/ml, or 15 to 25 mg/ml. The sum of the parabens may, in some embodiments, be present at a concentration of 0.1 to 5 mg/ml, or 0.5 to 5 mg/ml, or 1 to 3 mg/ml. Klucel™ HXF PH (Ashland Chemical) is a commercially available hydroxypropyl cellulose, and methyl paraben and propyl paraben are available commercially as well (Ruger Chemical).

In some embodiments, the oral formulation has from about 25% to at least about 50% metamizole; 0.5 to 10% of one or more thickening agents; and otherwise contains water and optionally other pharmaceutically acceptable excipients (including, without limitation, one or more polymeric excipients, a preservative, such as an antioxidant, such as sodium metabisulfite, and/or an antimicrobial agent, a buffer to maintain the desired pH, and a flavoring).

A flavoring agent, when employed, may include any natural, nature-identical, and/or artificial flavoring substance (s) that alters the flavor of the pharmaceutical composition to increase acceptance by the intended equine recipient of the administered unit dose. In some embodiments, the pharmaceutical composition contains a flavoring agent in a range of 0.5% w/w to 10% w/w, of 1% w/w to 5% w/w, and preferably of about 2% w/w. In some embodiments, the flavoring agent of the pharmaceutical composition is apple.

The pharmaceutical formulation may further include one or more additional excipients that improve the properties or function of the formulation. For example, in some embodiments the pharmaceutical formulation contains one or more preservative agents. In some embodiments, the pharmaceutical formulation contains one or more preservative agents selected from the group consisting of alcohol, benzyl alcohol, bronopol, chlorbutol, chlorocreson, a paraben such as, without limitation, butyl, methyl or propyl paraben, phenol, phenylethanol, sodium benzoate, potassium sorbate, sorbic acid, glycerin, and propylene glycol. In some embodiments, the pharmaceutical composition contains a preservative agent in a range of 0.05% w/w to 0.5% w/w, typically the amount is about 0.2% w/w. In some embodiments, the pharmaceutical composition contains at least two preservative agents such as methylparaben and propylparaben. In other embodiments, the pharmaceutical compositions contain a preservative that is an antioxidant, such as sodium metabisulfite. Various formulations provided herein include sodium metabisulfite, methylparaben, and propylparaben.

The pharmaceutical formulation provided herein may further comprise a buffering agent, such as a buffering salt and/or a pH buffering additive. In some embodiments, the pharmaceutical composition contains a preservative agent with solvent properties, such as propylene glycol, at a higher concentration, for example, at a concentration of 10 mg/ml to 500 mg/ml, or 10 mg/ml to 300 mg/ml, or 50 mg/ml to 300 mg/ml, or 50 mg/ml to 200 mg/ml, or 50 mg/ml to 150 mg/ml.

In some embodiments, the oral formulation provided herein comprises an aqueous solution, pH 7.5-8, comprising 250-750 mg/mL metamizole sodium monohydrate, 5-15 mg/ml xanthan gum, and 50-150 mg/ml propylene glycol. In some embodiments, the oral formulation comprises 1-50 mg/ml, 1-30 mg/ml, 5-30 mg/ml, 5-20 mg/ml, or 10-20 mg/ml benzyl alcohol.

In some embodiments, the oral formulation provided herein comprises an aqueous solution, pH 7.8, comprising 500 mg/mL metamizole sodium monohydrate, 10 mg/ml xanthan gum, and 100 mg/ml propylene glycol. In some embodiments, the formulation may comprise 15 mg/ml benzyl alcohol.

The present disclosure further relates to processes for preparing the new pharmaceutical formulations provided herein. In some embodiments, the process for the preparation of the pharmaceutical formulation comprises a first step of heating 30% of the water to between 60° C. and 70° C., in a first container. The heated water in the first container is then mixed at a high speed. Metamizole is then added to the heated water and mixed until dissolved. The temperature of the mixture is then reduced to between 50° C. and 60° C. A first preservative agent is then added to the mixture and mixed until dissolved, followed by the addition of a second preservative agent which is also mixed until dissolved. A flavoring agent is then added to the mixture and mixed until fully incorporated into the mixture. The gelling agent is then added to mixture and mixed for 5 minutes to create a slurry. In a separate container, the remaining 70% of the water is maintained at a temperature less than 21° C. and is mixed at low speed. The slurry from the first container is then added to the water of the second container and mixed until a gel forms.

In some embodiments, a thickening agent is added to at least one of the first and second containers prior to adding the slurry to the second container. In some embodiments, a thickening agent is added to the second container before and/or after the gel forms.

The oral gel pharmaceutical formulation provided herein may have the advantage of physical properties that provide a composition that is easily administered using a needle-less syringe to a horse, where the gel's viscosity helps retain the administered amount in the horse's mouth until it is swallowed. The novel pharmaceutical formulation has the further advantage of providing a unit dose form of metamizole (amount of gel administered) that is therapeutically effective to treat an equine for pyrexia.

The pharmaceutical compositions provided herein may have the advantage of assuring appropriately viscous formulations containing therapeutically effective amounts of metamizole optionally in combination with a flavoring agent that increases tolerability to the equine subject intended for treatment. In various embodiments, the present disclosure provides gels that are stable for at least a day, a week, two weeks, or at least 30 days in-use, e.g., at room temperature and that are easily dosed and administered via needle-less syringe or other similarly facile mode of oral administration. In many embodiments, commercial products will comprise a container containing a plurality of doses (from about 3 to about 30, or about 3 to about 10, or about 3 to about 6, for example and without limitation) of a pharmaceutical composition provided herein, which products may be packaged and sold in a single container, whereby the user accesses and administers the doses via a syringe, which optionally may be packaged or sold with the pharmaceutical formulation. In some embodiments, the pharmaceutical composition may be stored, for example, in its unopened container, for up to 1 year or up to 2 years, without significant loss of efficacy.

In one aspect, the present disclosure thus provides a method of treating pyrexia in an equine comprising administering an oral formulation of a therapeutically effective dose of metamizole to an equine patient. The formulation does not have to be novel; as illustrated in the examples, orally administered metamizole prepared for IV administration can be orally administered instead in accordance with the present disclosure. However, novel formulations are provided that may offer significant benefit in administration and efficacy. While the unit dose forms used in the methods provided herein may be administered at any frequency, and while in some embodiments a single dose will provide the desired treatment, the methods provided herein also include repeat daily administration, including up to at least 3 times daily for up to at least 5 days. In various embodiments of these methods, the therapeutically effective dose is 30-35 mg/kg, and the unit dose is administered in a formulation in which metamizole is present at a w/w percentage of at least 25% and typically at least 50% of the formulation, enabling a unit dose to be in the range of 20-50 ml.

EXAMPLES

Example 1: Demonstration that Orally Administered Metamizole can Treat Pyrexia in Equines A study in four horses was conducted to demonstrate oral bioavailability of metamizole. The commercially available Vetalgina product (Intervet) for IV administration (sodium salt) was administered in accordance with the manufacturer's instructions. Plasma was collected prior to administration and at specified intervals for up to 48 hours. Horses underwent a washout period, and then were administered the active ingredient (metamizole sodium monohydrate) in a water slurry to the horses' stomach via nasogastric intubation. Plasma was collected again prior to intravenous administration and at specified intervals for up to 48 hours. Horses were treated with matched doses on a milligram per kilogram basis for both test articles. Plasma was assayed for the primary metabolite of metamizole sodium, 4-methylaminoantipyrine (4-MAA). The results demonstrated comparable bioavailability between the orally and parenterally administered metamizole, as shown in FIG. 1.

A second pilot study was conducted to demonstrate efficacy of orally administered metamizole. Metamizole, as an active ingredient, was formulated into a simple gel for oral administration and dosed at 30 mg/kg body weight. Eight horses with naturally occurring respiratory infections were provided. The temperatures of the horses were monitored. Horses selected for this study demonstrated a consistent temperature ≥102.0° F. for 6 hours. Horses were treated up to three times with an oral formulation of metamizole sodium. Rectal temperature was monitored to determine response to treatment. All 8 horses demonstrated a clinically significant improvement, as defined by a ≥2° F. decrease in temperature, or a return to normothermia (≤101.0° F.) 6 hours following dose administration, in rectal temperature following oral administration of metamizole sodium. Table 1 describes the findings for the first dose administered. Pyrexia returned at timepoints appropriate for the drug's plasma residence time. This study demonstrated that oral administration of metamizole sodium is effective in controlling fever in adult horses.

TABLE 1

Responder/Non-responder at Hour 6 Following the First Dose Treated Patients

| Patient ID | Temperature at Hour 0 | Temperature at Hour 6 | Response |
| --- | --- | --- | --- |
| 706 | 103.5 | 101.0 | Yes |
| 711 | 102.2 | 98.6 | Yes |
| 712 | 102.7 | 100.8 | Yes |
| 713 | 102.0 | 99.8 | Yes |
| 717 | 102.0 | 99.1 | Yes |
| 719 | 102.2 | 99.8 | Yes |
| 720 | 102.3 | 98.7 | Yes |
| 722 | 103.9 | 101.1 | Yes |

Example 2: Oral Formulation of Metamizole 220 grams of purified water is placed into a first container and heated to 60-70° C. while undergoing mixing at a high speed. 249 grams of metamizole sodium monohydrate is added to the heated water and mixed until completely dissolved. The temperature of the mixture is reduced to 55-60° C. 1.8 grams of methyl paraben is added to the first container and mixed until completely dissolved. 0.2 grams of propyl paraben is then added to the first container and mixed until completely dissolved. 20.4 grams of Kkucel™ HXF PH hydroxypropylcellulose is then added to the first container and mixed for 5 minutes to create a slurry. 514 grams of purified water is then added to a second container and mixed at a low speed while maintaining the temperature of the purified water in the second container to below 22° C. The slurry from the first container is added to the second container and mixed until a gel forms.

Two lots (one of about 1 kg and the other over 2 kg, with metamizole sodium monohydrate present in an amount of at least 244 mg/ml) were manufactured generally in accordance with the above process, and aliquots placed in 200 cc amber bottles (~140-160 ml per bottle) and stored at 40° C., 75% relative humidity for an initial assessment of stability. After one month, both lots demonstrated greater than 94% label claim, with one lot at 99% label claim.

The oral formulation of metamizole was an aqueous formulation comprising 249 mg/ml metamizole sodium monohydrate, 20.4 mg/ml Kkucel™ HXF, 1.8 mg/ml methyl paraben, and 0.2 mg/ml propyl paraben.

Example 3: Treatment of Pyrexia

A horse is treated for pyrexia with an oral gel formulation of metamizole sodium monohydrate at the dose of 35 mg/kg. For example, a horse weighing 1000 lbs (454 kg) receives ~16 g of metamizole sodium monohydrate in a dose of about 30 ml, and the concentration of the metamizole in the dose is about 500 mg/ml.

In another instance, a horse is treated for pyrexia with an oral gel formulation of metamizole sodium monohydrate at a dose of 30 mg/kg. In various instances, horses are treated for pyrexia with an orally administered gel formulation of metamizole sodium monohydrate at a dose of 30-35 mg/kg, and the this dose is administered from once to no more than up to 3 times daily, for one to up to 5 days.

Example 4: Treatment of Pyrexia with Oral Formulation of Metamizole

A two-phase study to determine the efficacy of oral metamizole in mature horses was conducted as follows. In the first phase, 9 horses with clinical signs of infectious disease were enrolled. Once a horse had a single temperature reading of ≥102.0° F., it was enrolled in the study and dosed orally within 1 hour with metamizole sodium monohydrate at 30 mg/kg.

In the second phase, 8 horses with clinical signs of infectious disease were enrolled. Once a horse had a single temperature reading of ≥102.0° F., it was enrolled in the study and dosed orally within 1 hour with metamizole sodium monohydrate at 40 mg/kg.

The oral formulation of metamizole used for both phases was an aqueous formulation comprising 500 mg/ml metamizole sodium monohydrate, 10 mg/ml xanthan gum, and 100 mg/ml propylene glycol, and 15 mg/ml benzyl alcohol. The formulation was adjusted to pH 7.8 using sodium hydroxide.

For both phases, rectal temperature was monitored at pre-determined intervals. Horses were redosed based on rectal temperature and minimum dosing intervals up to five additional times, for a total of six doses. Fever was required for redose with metamizole. Primary responders were defined as horses where the temperature at Hour 6 decreased either ≥2° F. from Hour 0 or decreased to ≤101.0° F. after Dose 1. Table 2 shows the results of the study for all doses.

TABLE 2

Responder/Non-responder at Hour 6 Following All Doses

| Patient ID | Treatment Group | Dose 1 | Dose 2 | Dose 3 | Dose 4 | Dose 5 | Dose 6 |
|---|---|---|---|---|---|---|---|
| 798 | 30 mg/kg | N | N | Y | Y | ** | Y |
| 799 | 30 mg/kg | Y | Y | Y | | | |
| 811 | 30 mg/kg | Y | Y | Y | Y | Y | |
| 813 | 30 mg/kg | N | Y* | Y | Y | Y | Y |
| 814 | 30 mg/kg | Y | Y* | Y | N | N | Y |
| 815 | 30 mg/kg | Y | N | Y | N | N | Y |
| 816 | 30 mg/kg | Y | Y | N | Y | N | N |
| 817 | 30 mg/kg | Y | Y* | N | N | Y | |
| 818 | 30 mg/kg | Y | Y | Y | Y* | Y | |
| 821 | 40 mg/kg | Y | | | | | |
| 823 | 40 mg/kg | N | Y | Y | Y | N | Y |
| 824 | 40 mg/kg | Y | Y | Y | | | |
| 826 | 40 mg/kg | Y | Y | N | Y | Y | N |
| 827 | 40 mg/kg | Y | Y | | | | |
| 829 | 40 mg/kg | Y | Y | Y | Y | Y | N |
| 830 | 40 mg/kg | Y | Y | | | | |
| 831 | 40 mg/kg | Y | Y | Y | Y | | |

*Patients with baseline temperature less than 102° F.
** Baseline temperature = 101.2° F., therefore this visit was excluded from response status assessment In phase 1 (30 mg/kg), 7/9 horses were defined as primary responders after Dose 1. In Phase 2 (40 mg/kg), 7/8 horses were defined as primary responders after Dose 1. Adverse events were consistent with the underlying infections required for enrollment.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for treating an equine with pyrexia, said method comprising orally administering a therapeutically effective dose of metamizole to said equine, wherein the dose is orally administered as a gel or paste, wherein the gel or paste comprises metamizole at a concentration of 400 mg/ml to 600 mg/ml, xanthan gum at a concentration of 5 mg/ml to 20 mg/ml, and propylene glycol at a concentration of 50 mg/ml to 200 mg/ml.

2. The method of claim 1, wherein said dose is in the range of 25 mg metamizole per kg of equine subject weight (mg/kg) to 40 mg/kg.

3. The method of claim 1, wherein said gel or paste comprises 500 mg/ml metamizole sodium monohydrate, 10 mg/ml xanthan gum, and 100 mg/ml propylene glycol, in an aqueous solution.

4. The method of claim 1, wherein the equine's temperature is reduced by at least 1° C. six hours after administration of metamizole.

5. The method of claim 1, wherein the metamizole is metamizole sodium monohydrate.

6. The method of claim 1, wherein the gel or paste has a viscosity of 200 cps to 20,000 cps at 25° C.

7. The method of claim 1, wherein said dose is 40 mg metamizole per kg of equine subject weight (mg/kg).

8. The method of claim 7, wherein the concentration of metamizole in said gel or paste is 500 mg/ml.

9. The method of claim 8, wherein a syringe is used to orally administer the gel or paste.

10. The method of claim 7, wherein the therapeutically effective dose of metamizole is administered up to three times daily for up to five days.

11. The method of claim 1, wherein the therapeutically effective dose of metamizole is administered up to three times daily for up to five days.

12. The method of claim 2, wherein said dose is 40 mg metamizole per kg of equine subject weight (mg/kg).

13. The method of claim 12, wherein a syringe is used to orally administer the gel or paste.

14. The method of claim 12, wherein the therapeutically effective dose of metamizole is administered up to three times daily for up to five days.

15. The method of claim 2, wherein said gel or paste comprises 500 mg/ml metamizole sodium monohydrate, 10 mg/ml xanthan gum, and 100 mg/ml propylene glycol, in an aqueous solution.

16. The method of claim 4, wherein said gel or paste comprises 500 mg/ml metamizole sodium monohydrate, 10 mg/ml xanthan gum, and 100 mg/ml propylene glycol, in an aqueous solution.

17. The method of claim 6, wherein said gel or paste comprises 500 mg/ml metamizole sodium monohydrate, 10 mg/ml xanthan gum, and 100 mg/ml propylene glycol, in an aqueous solution.

* * * * *

UNITED STATES PATENT AND TRADEMARK OFFICE
CERTIFICATE OF CORRECTION

PATENT NO. : 10,682,337 B2
APPLICATION NO. : 15/554568
DATED : June 16, 2020
INVENTOR(S) : Emily Sundman Page 1 of 1

It is certified that error appears in the above-identified patent and that said Letters Patent is hereby corrected as shown below:

In the Claims

Claim 12, Column 14, Line 37 should read --12. The method of claim 3, wherein said dose is 40 mg--

Signed and Sealed this
Fifteenth Day of September, 2020

Andrei Iancu
*Director of the United States Patent and Trademark Office*